United States Patent [19]

Kalt

[11] Patent Number: 4,966,590
[45] Date of Patent: Oct. 30, 1990

[54] IV CLAMP WITH MEMBRANE DRESSING

[75] Inventor: Glenda G. Kalt, Boca Raton, Fla.

[73] Assignee: Kalt Medical Corporation, Boca Raton, Fla.

[21] Appl. No.: 283,827

[22] Filed: Dec. 13, 1988

[51] Int. Cl.⁵ .............................................. A61M 25/02
[52] U.S. Cl. ............................. 604/180; 128/DIG. 26
[58] Field of Search ....................... 604/180, 179, 174; 128/DIG. 26, DIG. 15, DIG. 16; 24/306, 442

[56] References Cited

U.S. PATENT DOCUMENTS

| | | |
|---|---|---|
| 2,221,758 | 11/1940 | Elmquist . |
| 2,273,873 | 2/1942 | Klein . |
| 2,707,953 | 5/1955 | Ryan . |
| 2,735,432 | 2/1956 | Hudson . |
| 2,949,443 | 8/1960 | Merriam et al. . |
| 3,046,989 | 7/1962 | Hill . |
| 3,059,645 | 10/1962 | Hasbrouck et al. . |
| 3,161,199 | 12/1962 | Shaw . |
| 3,288,136 | 11/1966 | Lund . |
| 3,324,853 | 6/1967 | Czorny et al. . |
| 3,630,195 | 12/1971 | Santomieri . |
| 3,667,250 | 7/1972 | Thomas . |
| 3,696,920 | 10/1972 | Lahay . |
| 3,702,612 | 11/1972 | Schlesinger . |
| 3,782,383 | 1/1974 | Thompson et al. . |
| 3,826,254 | 7/1974 | Mellor . |
| 3,834,380 | 9/1974 | Boyd . |
| 3,918,446 | 11/1975 | Buttaravoli . |
| 3,972,321 | 8/1976 | Proctor . |
| 4,018,221 | 4/1977 | Rennie . |
| 4,074,397 | 2/1978 | Rosin . |
| 4,088,136 | 5/1978 | Hasslinger . |
| 4,122,857 | 10/1978 | Haerr . |
| 4,142,527 | 3/1979 | Garcia . |
| 4,165,748 | 8/1979 | Johnson . |
| 4,181,127 | 1/1980 | Linsky et al. . |
| 4,221,215 | 9/1980 | Mandelbaum ............... 128/DIG. 26 |
| 4,324,237 | 4/1982 | Buttaravoli . |
| 4,329,984 | 5/1982 | Kervin . |
| 4,333,468 | 6/1982 | Geist . |
| 4,341,207 | 7/1982 | Steer et al. . |
| 4,341,208 | 7/1982 | Gordon . |
| 4,416,664 | 11/1983 | Womack . |
| 4,417,710 | 11/1983 | Adair . |
| 4,485,809 | 12/1984 | Dellas . |
| 4,534,762 | 8/1985 | Heyer . |
| 4,583,976 | 4/1986 | Ferguson . |
| 4,617,017 | 10/1986 | Hubbard et al. . |
| 4,669,458 | 6/1987 | Abraham et al. . |
| 4,737,143 | 4/1988 | Russell ........................ 128/DIG. 26 |
| 4,744,355 | 5/1988 | Faasse, Jr. . |

FOREIGN PATENT DOCUMENTS 998901  10/1976  Canada .

OTHER PUBLICATIONS

"Product News", Description of Cath-Secure by M. C. Johnson Co., Inc.
Conmed Venigard Disposable Dressing brochures, Catalog Nos. 705-4431, 705-4432, 740-1440 and 745-1441.
The 3-M TEGADERM Transparent Dressing Brochure by the 3-M Company.
Dale Endotracheal Tube Holders for Oral Intubation Instruction Sheet No. 507, Copyright 1985, Rev. 4/87.

Primary Examiner—Stephen C. Pellegrino
Attorney, Agent, or Firm—Dickstein, Shapiro & Morin

[57] ABSTRACT

A first clamp for holding an article to an object including a base for adhering the clamp to the object, a flap, and securing surfaces for securing the flap to the base with the article positioned therebetween and a resilient pad having an adhesive surface for contacting the article. Resilient adhesive surfaces are provided on the flap and base for contacting and adhering the article. A second clamp is adhered to the first clamp for holding a tube attached to the object from moving when the tube is accidently pulled or jerked.

40 Claims, 3 Drawing Sheets

IV CLAMP WITH MEMBRANE DRESSING

BACKGROUND OF THE INVENTION

The present invention relates in general to a clamp for holding an article and more particularly to a medical clamp for holding a tube or IV needle to a patient's body.

It is often necessary to clamp external and mesentery tubes and lines to a medical patient's body. The types of tubes that are involved in medical applications include, for example, feeding tubes, naso-gastric tubes, chest tubes, foley catheter as well as condom catheter tubes, dialysis tubes, endotracheal tubes, pressure monitoring devices, angiocath and heparin lock set tubes, as well as other tubes and lines used to introduce fluids into the body intravenously or to introduce oxygen into the mouth or nose of a patient.

It is important that a tube clamp holds the tube or line firmly. Any movement of the tubes or lines may cause discomfort to the patient. It is often necessary to remove the tube and replace it with another or to adjust the position of the tube or line. Therefore, it is desirable that the clamp be releasable so that the tube or line may be unclamped and reclamped without removing or replacing the entire clamp structure.

U.S. Pat. No. 3,826,254 discloses a clamp comprising an adhesive pad which folds back over itself to adhere a tube.

U.S. Pat. No. 4,165,748 discloses a tube clamp formed in one piece and adhered to a patient's body and having a center portion which folds around and clamps the tube by adhering to itself.

U.S. Pat. No. 4,333,468 discloses a clamp having a base having two raised portions to form between them a transverse groove. A tube is accepted to lie in the groove and a flap permanently affixed to the base at one end is extendable over the tube. A pressure sensitive adhesive covers the raised portions and the groove of the base as well as the flap underside. The flap is pressed onto the raised portions and the tube to adhere and clamp the tube in the groove.

Each of the foregoing clamps suffers from the disadvantage that a slight rotation or translation of the tube tends to break the adhesive bond. Thus, secure holding of the tube is not effected.

U.S. Pat. No. 3,834,380 discloses a clamp including a slit tube which receives a rod-like article and is kept closed by a flap attached to the tube at one end and secured at the other end. The tube is flexible and may be resilient. However, this device is unduly bulky and may cause discomfort to the patient. Moreover, the device tends to lift the clamp tape off of the patient which causes further discomfort. This device also is insufficiently flexible for use in areas of the body where movement is likely and flexibility is desired. Such areas include the head and joint areas. This inflexibility may result in a tube being held in a wrong position. Further, this device depends on friction for holding a tube, and is therefore dependent upon the surface properties of the article or tube to be held to effect such a friction bond. If the surface of the article to be held is "slippery" relative to the material of the slit tube, the holding effect will be poor. A final disadvantage of this device is that only a small range of sizes of tubes may be held for a given slit tube size.

Haerr, U.S. Pat. No. 4,122,857 discloses a substantially rectangular pad made of soft, strong, flexible, foam material provided with a secure flap by which an article such as a catheter tube or the like may be anchored to the pad which, in turn, is adapted to be adhesively affixed to the skin of the patient.

SUMMARY OF THE INVENTION

The present invention alleviates to a great extent the disadvantages of prior devices by providing a first clamp for holding an article to an object including a base means for adhering the clamp to the object, a flap, securing means for securing a flap to the base means with the article positioned therebetween, and resilient pad means having an adhesive surface for contacting the article. In one aspect of the invention, the securing means includes a first holding means for holding a first portion of the flap and a second holding means for holding a second portion of the flap. The second holding means is spaced along the flap from the first holding means a sufficient distance for the article to lie between them. The resilient pad means is deformable such that slight rotational or translational movement will deform the pad rather than break the adhesive bond between the pad and the article. A second clamp is also provided for holding a tube connected to the object firmly in place relative to the first clamp.

In another aspect of the invention, the base means has a base window formed therein for positioning the clamp on the patient with the IV puncture positioned to be viewed through the window.

It is an object of the present invention to provide a clamp for holding an article.

It is a further object of the present invention to provide a clamp having a resilient adhesive pad in contact with the held article to inhibit the breaking of the adhesive bond as a result of rotational or translational movement of the article.

It is another object of the invention to provide a medical clamp to releasably hold a tube or line and to allow removal of the tube or line and repositioning of the tube or line without removal of the clamp from the patient's body.

It is yet another object of the invention to provide a medical clamp yielding the foregoing advantages and that effectively holds a tube against transverse and rotational movement.

It is still another object of the present invention to provide a medical clamp yielding the foregoing advantages and that is simply and economically constructed.

It is still further object of the present invention to provide a medical clamp yielding the foregoing advantages and that can clamp a variety of sizes of tubes.

DETAILED DESCRIPTION OF THE PREFERRED EMBODIMENTS

As referred to herein, the inner surfaces of various component parts of the preferred embodiments of the present invention are those surfaces oriented towards the object to which the clamp is adhered. Similarly, the outer surfaces of the various component parts of the preferred embodiment are those surfaces oriented away from such object. Such object may be any object but for medical clamps will most likely be the patient's skin, the patient's clothing, bandages, casts or the like.

Figure 3:
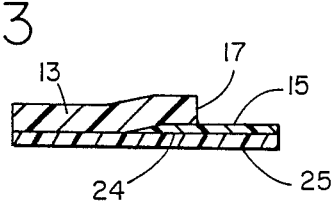
FIG. 3 is a view taken along Section line III—III of FIG. 4 is a view like FIG. 1 illustrating an alternate arrangement for clamping a needle and tube.

Referring now to FIGS. 1 through 5, therein is shown a medical clamp, generally designated by reference numeral 10, according to a preferred embodiment of the present invention. In the preferred embodiment, the clamp 10 is particularly suitable for holding an IV tube 22 to the skin of a medical patient. The base means for adhering clamp 10 to the patient includes a base 12 that is preferably composed of an adhesive, stretchable, polymer material such as is marketed by Conmed Corporation under the registered trademark "MACROLYTE", or an adhesive, stretchable, hypoallergenic foam material marketed by 3M Company under the registered trademark "MICROFOAM" or medical grade tape such as 3M1527L marketed by 3M Company under the registered trademark "Transpore". Base 12 is coated on its inner surface 24, with a medical grade adhesive, preferably a hypoallergenic synthetic acrylic pressure sensitive adhesive. A protective liner 25 is provided to extend over and protect the inner surface 24 and membrane 15 until the clamp is used. The base 12 includes window frame portion 13 forming a window opening 17. A sterile, breathable, clear, waterproof, membrane 15 extends over the window opening 17 and overlaps and is adhered to the window frame 13 on its inner surface 24 as shown in FIG. 3. A membrane dressing marketed by 3M Company under the trademark "TEGADERM" or a transparent dressing marketed by Johnson & Johnson, Inc. under the trademark "BIOCLUSIVE" are suitable to use for the membrane 15. The use of a membrane 15 with the window frame 13 seals and protects the skin puncture 90 by the needle 91, which extends through the membrane 15 at puncture hole 18. The arch 13 of clamp 10 is wider near flap 20 to give arch 13 structure that is less inclined to be pulled away from the skin.

Figure 1:
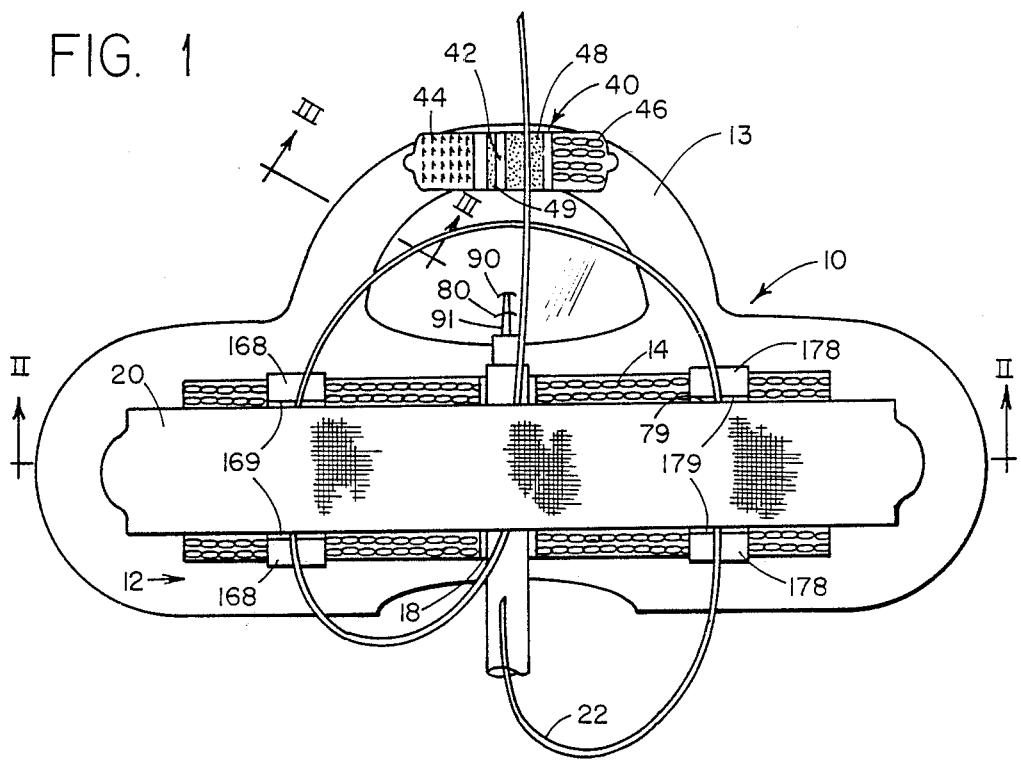
FIG. 1 is a plan view of a preferred embodiment of a clamp according to the present invention.
Figure 2:
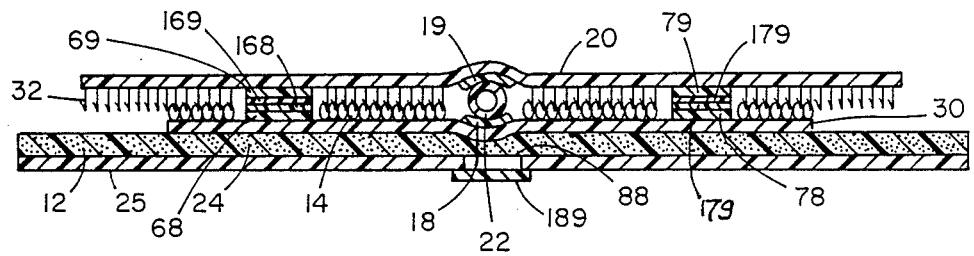
FIG. 2 is a view taken along section line II—II of FIG. 1.

As shown in FIG. 1, the flap 20 extends outside the needle 91 and is secured both to the base 12 and to various looped portions of the tube 22 by securing means. In the first preferred embodiment, the securing means includes a hook and loop fastening material 32 and 30 (see FIG. 2) as described in more detail below. The flap 20 includes a hook base fabric into which is woven hooks 32 of the securing means.

The loop pad 14 is composed of a loop material that includes a loop fabric 30 which is woven into a base fabric (not shown). The pad 14 is adhered to the base 12 by medical grade adhesive. The loop pad 14 is adapted to mate with a hook pad (FIG. 2) to secure the flap 20 to the base 12. The tube 22 extends along the resilient adhesive pads 18 and 19 (see FIG. 2) and is looped through adhesive pads 19, 168, 178 and between the flap 20 and the base 12.

The hook and loop materials are available from 3M Company under the registered trademark "Scotchmate". Resilient adhesive pads 18, 68 and 78 (see FIG. 2) are formed by applying a hot melt adhesive to the loop fabric 30 such that the applied adhesive extends up slightly above the top of the loops. Resilient pads 19, 69 and 79 (FIG. 2) are formed by applying a hot melt adhesive to the hook fabric 32 such that the applied adhesive also extends up slightly above the hooks. When the hot melt adhesive cools and cures, it forms a resilient pad with an adhering outer surface. A resilient adhesive pad 88 is provided on the inside surface 24 of base 12 for use as described below with respect to FIG. 4. Liners 119 (see FIG. 5), 169, 179 and 189 are provided to protect the resilient pads prior to use. Medical grade hot melt adhesives suitable for this purpose include numbers DD5800, DD5900, DD5914 available from H. Fuller Adhesive Company. Preferably, the applied hot melt adhesive, when set up, or cured, will extend about one sixteenth of an inch above the loop or hook material surface.

The medical clamp 10 further includes a second tube securement clamp 40. The clamp is formed from a separate piece of material that is adhered to the window frame 13 by an adhesive layer formed on the inside surface of the clamp (not shown). The second clamp includes a hook portion 44, loop portion 46, and a central portion 42 defined between the hook 44 and loop 46 portions. The inside surface below portions 44 and half of portion 42 adjacent hook portion 44 does not include an adhesive layer. As a result, the hook portion 44 and part of the center portion 42 may easily fold over the remaining half of the central portion 42 and loop portion 46 and thus mate to the hook and loop portions 44, 46.

The second clamp 40 operates to hold the tube 22 longitudinally across central portion 42 without using a separate piece of medical tape. All that is required is for the hook portion 44 to be folded over the tube 22 such that the hook 44 contacts loop base 46 (see FIG. 4). Accordingly, the tube is flexibly held in central portion 42 so that stress, pulls or sudden jerks on the tube will not move the needle 91 as a result of the combined holding of first clamp 20 and second clamp 40. When the IV needle is being removed, adjusted or inserted, the second clamp 40 ensures that accidents will be avoided. The flap is constructed of a hypoallergenic foam layer (described above). One end of the foam layer is located below loop portion 46, and has an adhesive layer for attaching to the window frame 13. The hook and loop pads are attached to the foam by means of an adhesive layer.

The material of central portion 42 can also include a hot melt adhesive strip 48, that is formed longitudinally along the central portion 42 to one side of fold line 49. When the tube 22 is thus placed across central portion 42, it contacts adhesive strip 48 in order to flexibly secure tube 22 to the second clamp 40.

In the preferred embodiment, the loop material has been provided to face outwards because the loop material is typically softer than the hook material and will not discomfort the patient if her skin should rub against it.

With reference to commonly owned U.S. patent application No. 227,784, filed Aug. 3, 1988, the disclosure of which is incorporated by reference, it has been found that the utilization of a resilient adhesive pad in contact with an IV needle structure provides a secure means for holding the tube 22 or other structure against rotational or translational movement. This may be because in use the resilient material tends to deform and twist through its thickness and move with the tube when the tube is urged to rotate slightly or to translate slightly. Because the resilient material deforms, the bond of the adhesive with the tube is stressed to a lesser degree and is less likely to be broken. Significant deformation must occur before the resilient material will resist further deformation with such a force that the adhesive bond between the pad and the tube is broken. Accordingly, significant movement of the tube is possible prior to the breaking of the adhesive bond.

Conversely, in prior clamps where no resilient adhesive pads are provided, any rotational or translational movement of the tube, with respect to the clamp adhesive surfaces may be caused by bumping the tube and may likely result in breaking the adhesive bond holding the tube. The adhesive surface of clamps formed of a continuous foam material covered with an adhesive layer tends to pull away from and separate from the tube or IV clamp due to the stretching of the adhesive surface.

Figure 4:
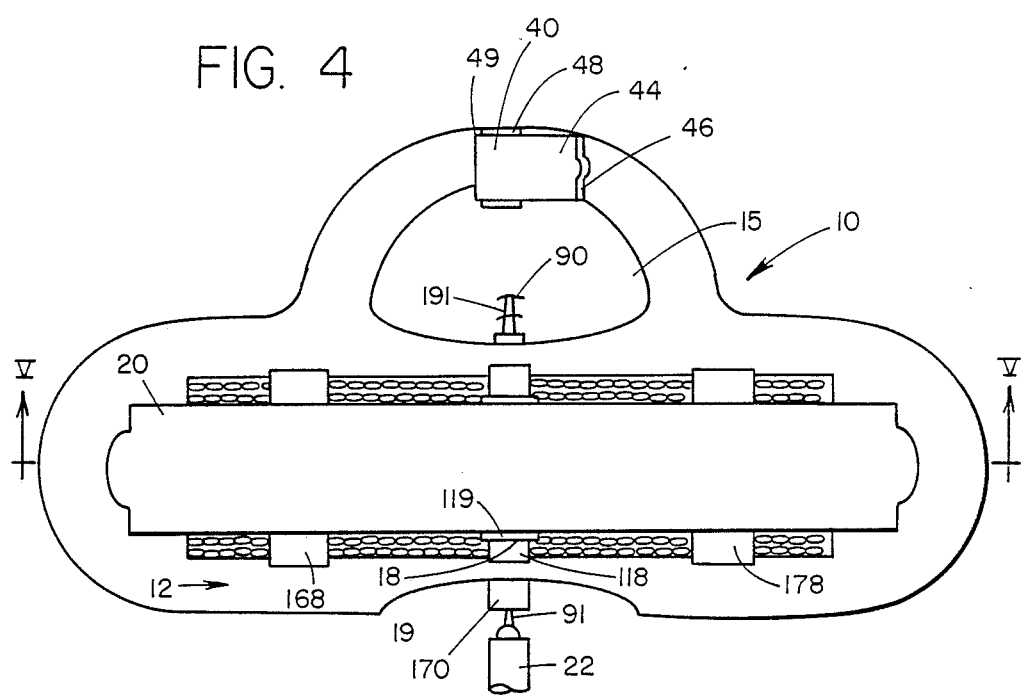
Figure 5:
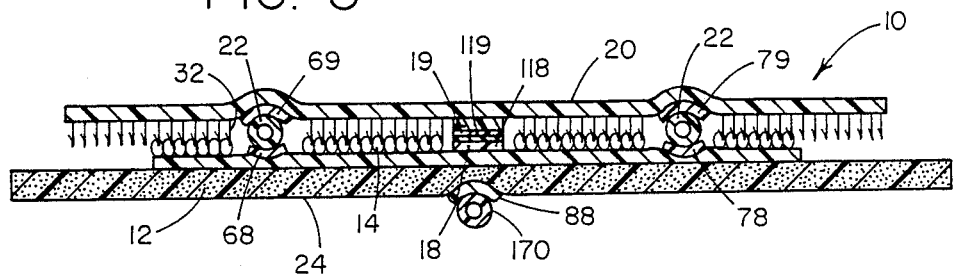
FIG. 5 is a view taken along section line V—V of FIG. 4.

Refer now to FIGS. 4 and 5 there being shown clamp 10 used in a different manner. In FIGS. 4 and 5, clamp 10 is folding an IV 170 between the base and the skin of the patient The needle 191 of the IV 170 extends under the clear membrane 15 to puncture the flesh at puncture 90. The IV needle 91 is inserted into a self sealing type IV needle 170. Tube 22 is held by adhesive pads 168, 178, of the base and 69 and 79 (FIG. 5) of the clamp 20, respectively. Moreover, the tube 22 is secured by the second clamp 40 which is shown in it's folded over position such that the loop portion 46 contacts hook portion 44. The tube is held by adhesive strip 48 located along one side of the fold line 49. IV 170 is held by resilient adhesive pad 88 (see FIG. 2) from which protective liner 189 (FIG. 2) has been removed. The tube 22 is looped around to lie over and between the resilient adhesive pads as well as within the second clamp 40 in the same manner as shown in FIG. 1 so as to provide further resilient holding of the tube and to decrease the likelihood of the IV 170 being moved upon inadvertent jostling of the tube 22. As a result of the additional holding of tube 22 by the pads 68, 78, 69 and 79 of the first clamp 20 and pad 48 of the second clamp 40, the adhesive pad 88 may alternately be dispensed with so that the adhesive surface 24 of the base 12 extends over and contacts the IV 170. Liners 118 and 119 (FIG. 5) are shown in place, protecting resilient adhesive pads 18 and 19 when not in use.

Figure 6:
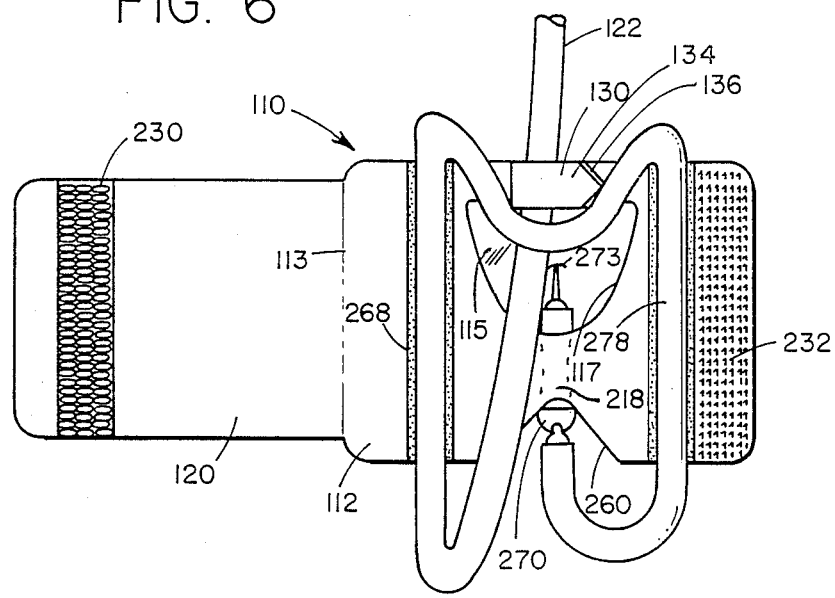
FIG. 6 is a plan view of an alternate embodiment of a clamp according to the present invention.

Refer now to FIG. 6 there being shown an alternate embodiment of the present invention, generally designated by reference numeral 110, particularly adapted for use with so called hepburn type locks for catheter needles. These locks are used when an intravenous needle is left in place over an extended time. These locks are also used in lines that are under increased pressure such as arterial lines. The locks act to provide a coupling for removably attaching various other needles and/or tubes for supplying medication, nourishment and the like. These locks may require access to locking mechanisms for operating the devices between open and closed positions and/or, these locks may be self sealing when the needle is removed.

Clamp 110 includes a base 112 having an adhesive lower surface protected with a liner which is removable for attaching the clamp 110 to the patient via base 112. The base substrate material has hook material 232 woven into it. Flap 120, which is adhered to the edge 113 of the base 112, includes loop material 230 woven into it. A clear membrane 115 similar in construction to membrane 15 discussed above, extends over window opening 117 forming in base 112 and over puncture 273 caused by the IV needle 270. Resilient adhesive pads 268 and 278, made of a hot melt adhesive, lie adjacent window opening 117. A second clamp 130 similar in construction to clamp 40 discussed in FIG. 2, secures tube 122 when a hook portion 134 located on the flap of clamp 130 is folded over to secure with loop portion 136. Tube 122 is thus positioned on pads 268 and 278 on an adhesive pad on second clamp 130, as well as on an adhesive pad 218 (see dotted lines) in order to provide increased support and isolation for the tube 122 and to protect the IV 270 from movement.

Slot 260 allows access to the actuator of a hepburn lock IV 270 if present. The resilient adhesive pad 218 (also composed of hot melt adhesive) is also present for holding the IV 270. Note that the loop material 230 engages the hook material 232 for holding the clamp shut. The resilient adhesive pad 218 thus functions to allow some movement of the IV 270 relative to the clamp through the twisting motion of the pad through its thickness. This results in increased comfort to the patient.

Figure 7:
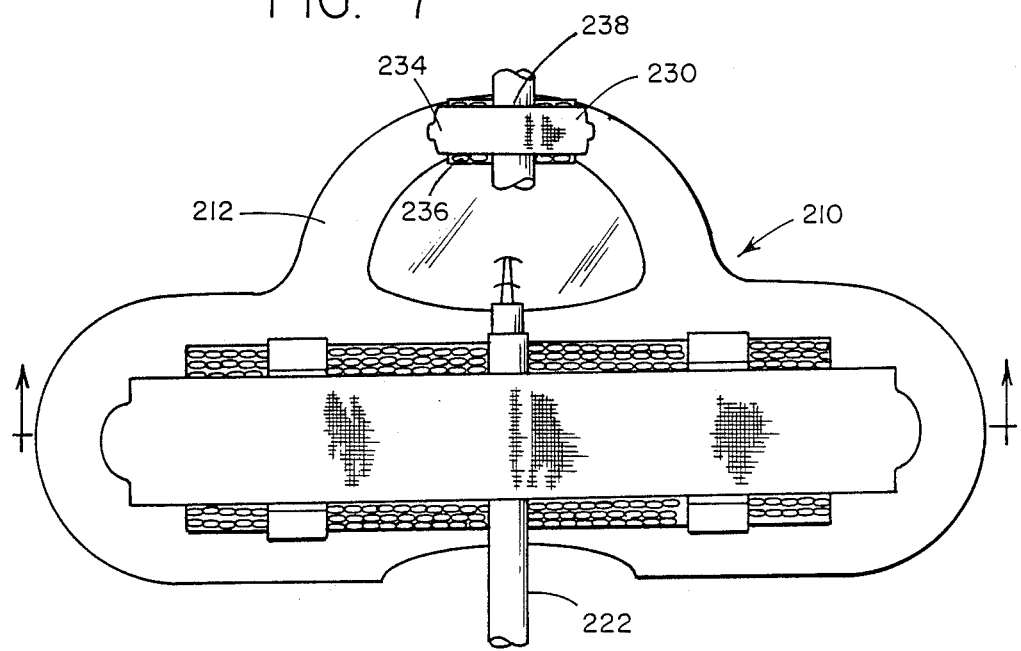
FIG. 7 is a plan view of an alternate embodiment of a clamp according to the present invention.

Refer now to FIG. 7 there being shown a clamp 210 showing an alternate embodiment of the present invention. In this embodiment the clamp 210 is suitable for holding an IV tube 222 to the skin of a patient. The arrangement and materials of clamp 210 is identical to the clamp 10 shown in FIG. 1 with the exception of second clamp 230.

The second clamp 230 consists of a base 236 made of a loop fabric woven into a base fabric having an adhesive inside surface (not shown). A flap 234 includes a hook portion which is adapted to mate with the loop pad base 236 in order to secure tube 222 to the base 212. Accordingly, the second clamp 230 provides a securing means for holding tube 222 in place against inadvertent jostling of the tube. The inclusion of a separate flap 234 rather than a fold-over flap results in reducing movement or pulling of base 212 when the flap 234 is separated from the loop pad base 236. Alternately, a hot melt adhesive layer 238 can be provided in the center of the loop pad base 236 in the same manner as described above.

In the preferred embodiments of the invention, a medical grade adhesive and a hook and loop material is provided to secure the flap to the base However the present invention is not limited thereto, and other securing means may be used. For example hook material may be used in conjunction with a foam and fabric material. This is sometimes preferable if a somewhat lower holding force is required between the flap and the base. Moreover, the fabric and foam material may be more breathable and stretchable than a plastic base material and allow greater air transfer through the clamp to the patient's skin when used thereon.

Also, the clamp, as described in the preferred embodiments, is shown in a hospital setting, although as already pointed out, the clamps may be used in other settings, medical, medical related and non-medical, for holding articles to objects What is new and desired to be protected by Letters Patent of the United States is:

1. A clamp for holding an IV device, comprising:
base means having an arch portion defining a window opening;
membrane means covering said window opening and having a slot for allowing a needle for said IV device to puncture a patient's skin at a point located under said membrane means;
flap means for covering a tube for said IV device;
securing means for securing said flap means to said base means; and
tube clamp means attached to said base means for holding said IV tube such that said IV device will not move when stress is applied to said IV tube.

2. The clamp of claim 1, wherein said base means has an adhesive inner surface for adhering said clamp to such skin of a medical patient.

3. The clamp of claim 2, wherein said membrane means has an outside surface which partially overlaps with said adhesive inner surface of said base means.

4. The clamp of claim 1, wherein said base means is made from a stretchable polymer material.

5. The clamp of claim 1, wherein said base means is made from an adhesive, stretchable hypoallergenic foam material.

6. The clamp of claim 1, wherein said arch portion borders said window opening.

7. The clamp of claim 6, wherein said arch portion is wider toward said flap means in order that said base means is less inclined to pull away from such skin.

8. The clamp of claim 6, wherein said tube clamp means is attached to said arch portion at a point above said window opening.

9. The clamp of claim 8, wherein said tube clamp means further comprises:
tube clamp base means for adhering to said arch portion;
tube clamp flap means for covering said IV tube;
tube clamp securing means for securing said tube clamp flap means to said tube clamp base means; and
tube clamp resilient pad means adhered to said tube clamp base means and having an adhesive surface for contacting said IV tube.

10. The clamp of claim 9, wherein said tube clamp flap means has a first end formed integrally with said tube clamp base means and a second end which is releasably secured to said tube clamp base means by said tube clamp securing means.

11. The clamp of claim 9, wherein said tube clamp securing means comprises hook and loop material formed on mutually aligned surfaces of said tube clamp base means and said tube clamp flap means.

12. The clamp of claim 9, wherein each end of said tube clamp flap means is releasably secured to said tube clamp base means.

13. The clamp of claim 1, wherein said membrane means is made from a sterile, breathable clear waterproof material.

14. The clamp of claim 1, further comprising a protective liner which extends over inner surfaces of said base means and said membrane means in order to protect said clamp when not in use.

15. The clamp of claim 1, wherein said securing means comprises a hook material and a loop fastening material.

16. The clamp of claim 15, further comprising an adhesive pad means which is applied to each of said hook and loop fastening materials such that said adhesive pad means extends up slightly above the top of said securing means.

17. The clamp of claim 16, wherein said adhesive pad means extends one sixteenth inch above the top of each of said hook and loop materials.

18. The clamp of claim 17, wherein said adhesive pad means is substantially resilient such that rotational and translational movement of said IV tube is hampered and said adhesive pad means deforms and twists through its thickness such that significant deformation of said clamp must occur before a bond between said IV device and said adhesive pad means is broken.

19. The clamp of claim 18, wherein said adhesive pad means is protected by a liner in order to cover said adhesive pad means when not in use.

20. The clamp of claim 1, further comprising self-sealing needle means located between said flap means and said base means wherein said IV needle is inserted into one end of sid selfsealing needle means and an opposite end of said self-sealing needle means is inserted through said membrane into such skin of a medical patient.

21. The clamp of claim 20, wherein said base means and said flap means each have three mutually aligned resilient adhesive pads to provide resilient holding to said self-sealing needle means and a portion of said IV tube in order that said IV tube is looped around said clamp and reduces movement of said IV device when stress is applied to said IV tube.

22. The clamp of claim 1, wherein said flap means is adapted to cover an entire outside surface of said base means.

23. A clamp for holding an IV device comprising:
base means having an adhesive inner surface and defining a window opening;
membrane means extending over said window opening in order to form a sterile, breathable, clear waterproof covering for said window opening;
flap means releasably secured to said base means;
resilient pad means attached to said base means and flap means wherein said flap means covers a tube and a needle of said IV device and holds said IV tube and said IV needle against rotation or translational movement as said resilient pad means tends to deform and twist through its thickness; and
tube clamp means adhered to said base means for holding a portion of said IV tube to said base means.

24. A clamp for holding an IV device to an object comprising:
base means having a window opening for adhering said clamp to such object;
a membrane covering said window;
a flap;
securing means for securing said flap to said base means with an IV tube positioned therebetween;
resilient pad means adhered to said flap and having an adhesive surface for contacting said positioned article such that an IV needle attached to said IV tube is inserted through said membrane and into such object; and
tube clamp means for holding a portion of said IV tube to said clamp.

25. A clamp for holding an IV device, comprising:
a base defining an arch portion having a window opening;
a membrane covering said window opening and having a slot;
a flap for covering a tube of said IV device; and
a securing device for securing said flap to said base.

26. The clamp of claim 25, wherein said base has an adhesive inner surface for adhering said clamp to a patient.

27. The clamp of claim 26, wherein said membrane has an outside surface which partially overlaps and mates with said adhesive inner surface of said base.

28. The clamp of claim 25, wherein said base is formed from a stretchable polymer type material.

29. The clamp of claim 25, wherein said base is formed from an adhesive stretchable hypoallergenic foam.

30. The clamp of claim 25, wherein said arch portion forms a border substantially around a perimeter of said window opening.

31. The clamp of claim 30, wherein said arch portion is wider toward said flap in order that said base is less inclined to pull away from a patient's skin upon opening said flap.

32. The clamp of claim 25, wherein said membrane is formed from a sterile, breathable, clear and waterproof material.

33. The clamp of claim 25, further comprising a protective liner which extends over said inner surface of said base and said membrane in order to protect said clamp when not in use.

34. The clamp of claim 25, wherein said securing device comprises a hook material and a loop material.

35. The clamp of claim 34, further comprising an adhesive pad applied to said hook and loop fastening materials, such that said adhesive pad extends up slightly above the top of said securing device.

36. The clamp of claim 31, wherein said adhesive pad extends substantially one-sixteenth inch above said hook and loop materials.

37. The clamp of claim 36, wherein said adhesive pad is substantially resilient wherein rotational and translational movement of said IV tube is hampered and said resilient material tends to deform and twist through its thickness such that significant deformation of said clamp must occur before a bond between said tube and said adhesive pad is broken.

38. The clamp of claim 37, wherein said adhesive pad is protected by liners in order to cover said adhesive pad when not in use.

39. The clamp of claim 25, further comprising a self-sealing needle located between said flap and said base such that when said IV needle is inserted into one end of said self-sealing needle an opposite end of said self-sealing needle is inserted through said membrane into such skin of a patient.

40. The clamp of claim 25, wherein said base and said flap each have three mutually aligned resilient adhesive pads in order to provide resilient holding of a self-sealing needle and a portion of an IV tube such that said IV tube may be looped around said clamp thereby reducing movement of said self-sealing needle and IV device when stress is applied to said IV tube.

* * * * *